US010087919B2

(12) United States Patent
Ito et al.

(10) Patent No.: US 10,087,919 B2
(45) Date of Patent: Oct. 2, 2018

(54) AIR COMPRESSOR WITH IMPROVED NOISE REDUCTION PERFORMANCE

(71) Applicant: Teijin Pharma Limited, Tokyo (JP)

(72) Inventors: Shinichi Ito, Iwakuni (JP); Hideo Nawata, Iwakuni (JP)

(73) Assignee: Teijin Pharma Limited, Tokyo (JP)

( * ) Notice: Subject to any disclaimer, the term of this patent is extended or adjusted under 35 U.S.C. 154(b) by 348 days.

(21) Appl. No.: 14/423,725

(22) PCT Filed: Sep. 19, 2013

(86) PCT No.: PCT/JP2013/076169
§ 371 (c)(1),
(2) Date: Feb. 25, 2015

(87) PCT Pub. No.: WO2014/051016
PCT Pub. Date: Apr. 3, 2014

(65) Prior Publication Data
US 2015/0204318 A1    Jul. 23, 2015

(30) Foreign Application Priority Data
Sep. 26, 2012    (JP) .................. 2012-212481

(51) Int. Cl.
*F04B 39/00*    (2006.01)
*F04B 39/16*    (2006.01)
(Continued)

(52) U.S. Cl.
CPC ..... *F04B 39/0061* (2013.01); *A61M 16/0063* (2014.02); *A61M 16/101* (2014.02);
(Continued)

(58) Field of Classification Search
CPC ........... A61M 16/0063; A61M 2205/42; F04B 39/0061; F04B 43/0736; F04B 43/026;
(Continued)

(56) References Cited

U.S. PATENT DOCUMENTS 4,124,091 A * 11/1978 Mizusawa ................ F01N 1/02
181/231
5,962,820 A * 10/1999 LePoutre ............... F02M 35/14
123/198 E
(Continued)

FOREIGN PATENT DOCUMENTS

CN        1638832 A      7/2005
CN      101737296 A      6/2010
(Continued)

OTHER PUBLICATIONS

Communication dated Nov. 13, 2015 from the European Patent Office in counterpart application No. 13841246.5.
(Continued)

*Primary Examiner* — Charles Freay
(74) *Attorney, Agent, or Firm* — Sughrue Mion, PLLC

(57) ABSTRACT

Provided is a compressor as a device which can solve a contradictory technical problem of installing an intake sound muffler while downsizing the device under a circumstance that installation of the intake sound muffler is indispensable to reduce intake noise of the compressor, and the compressor comprises: a first lid part provided with a small hole which forms an intake port of the compressor, the lid part constituting a portion of a cylindrical casing of the compressor; a cylindrical part; and a second lid part which forms a small chamber together with the first lid part, wherein the second lid part is provided with a suction nozzle for sucking air into the small chamber.

9 Claims, 3 Drawing Sheets

(51) Int. Cl.
 *A61M 16/00*   (2006.01)
 *F04B 35/01*   (2006.01)
 *F04B 39/12*   (2006.01)
 *F04B 43/02*   (2006.01)
 *F04B 43/073*   (2006.01)
 *A61M 16/10*   (2006.01)

(52) U.S. Cl.
 CPC .......... *F04B 35/01* (2013.01); *F04B 39/0055* (2013.01); *F04B 39/121* (2013.01); *F04B 39/128* (2013.01); *F04B 39/16* (2013.01); *F04B 43/026* (2013.01); *F04B 43/0736* (2013.01); *A61M 16/107* (2014.02); *A61M 2205/42* (2013.01)

(58) Field of Classification Search
 CPC ...... F04B 35/01; F04B 39/121; F04B 39/128; F04B 39/0055; F04B 39/16
 USPC .......................................... 181/229; 417/312
 See application file for complete search history.

(56) References Cited

U.S. PATENT DOCUMENTS

| | | | | |
|---|---|---|---|---|
| 5,996,734 | A * | 12/1999 | Lam | F02B 61/045 181/229 |
| 7,287,503 | B2 * | 10/2007 | Suzuki | F02M 35/024 123/184.53 |
| 7,381,032 | B2 * | 6/2008 | Osaka | F04B 39/0055 181/229 |
| 7,383,810 | B1 * | 6/2008 | Emley | F02M 35/1255 123/184.57 |
| 8,011,470 | B2 * | 9/2011 | Gurnee | A61G 10/026 181/229 |
| 2001/0031208 | A1 | 10/2001 | Chintamani et al. | |
| 2003/0180161 | A1 | 9/2003 | Hsiao | |
| 2006/0045768 | A1 * | 3/2006 | Chuang | F04B 39/128 417/415 |
| 2006/0137522 | A1 * | 6/2006 | Nishimura | A61M 16/10 95/96 |
| 2008/0085196 | A1 * | 4/2008 | Deubler | F04B 39/0055 417/312 |
| 2009/0025564 | A1 | 1/2009 | Kuwabara | |
| 2012/0121441 | A1 * | 5/2012 | Morrison | F04B 39/0066 417/53 |
| 2012/0304867 | A1 | 12/2012 | Watanabe et al. | |
| 2015/0316050 | A1 * | 11/2015 | Sharp | F04B 53/004 417/312 |

FOREIGN PATENT DOCUMENTS

| | | |
|---|---|---|
| EP | 1609499 A1 | 12/2005 |
| JP | 59-105979 A | 6/1984 |
| JP | 59-174380 U | 11/1984 |
| JP | 63-176677 A | 7/1988 |
| JP | 6-117375 A | 4/1994 |
| JP | 7-87884 B2 | 9/1995 |
| JP | 10-245203 A | 9/1998 |
| JP | 2000-179458 A | 6/2000 |
| JP | 2000-320458 A | 11/2000 |
| JP | 2003235982 A | 8/2003 |
| JP | 2005006731 A | 1/2005 |
| KR | 2003-0053198 A | 6/2003 |
| TW | 200417385 A | 9/2004 |
| WO | 2011/074192 A1 | 6/2011 |

OTHER PUBLICATIONS

Communication dated Feb. 11, 2016 from the Intellectual Property Office of Singapore issued in corresponding Application No. 11201502356Y.

Communication dated Dec. 1, 2015 from the Japanese Patent Office in counterpart application No. 2014-538608.

International Search Report for PCT/JP2013/076169 dated Nov. 5, 2013.

* cited by examiner

AIR COMPRESSOR WITH IMPROVED NOISE REDUCTION PERFORMANCE

TECHNICAL FIELD

The present invention relates to a muffling function and a dust-proof filtering function of a compressor, especially to a medical oxygen concentration device providing users such as patients having respiratory disease with oxygen-enriched air, and to a device used for realizing the reduction of the particularly problematic compressor noise during operation of the device.

BACKGROUND ART

In recent years, an increasing number of patients is suffering from respiratory diseases such as asthma, pulmonary emphysema, chronic bronchitis, etc. One of the most effective therapies for these diseases is oxygen inhalation therapy. Such oxygen inhalation therapy makes the patient inhale oxygen gas or oxygen-enriched air. An oxygen concentration device, liquid oxygen, an oxygen gas cylinder, etc. are known as the supply source, among which the oxygen concentration device is mainly used for home oxygen therapy due to its convenience in using and easiness in maintenance.

The oxygen concentration device concentrates oxygen present in the air at about 21% and supplies an oxygen-enriched gas. The oxygen concentration device includes a membrane-type oxygen concentration device utilizing a membrane which selectively permeates oxygen and a pressure-swing adsorption type oxygen concentration device utilizing an adsorbent which is capable of preferentially adsorb nitrogen or oxygen. The latter is mainly used because of the advantage that high-concentration oxygen of 90% or more can be obtained.

The pressure-swing adsorption type oxygen concentration device can continuously generate high-concentration oxygen-enriched gas by alternately repeating a pressurization/adsorption step to obtain an unadsorbed oxygen-enriched gas, wherein nitrogen is adsorbed on an adsorbent in an adsorbent cylinder filled with molecular sieve zeolite such as 5A type, 13X type, Li-X type, etc. as the adsorbent which preferentially adsorbs nitrogen over oxygen under a pressurized condition by supplying air compressed using a compressor, and a depressurization/desorption step in which the adsorbent is regenerated by reducing the pressure in the adsorbent cylinder to atmospheric pressure or lower and purging nitrogen adsorbed on the adsorbent.

Such an oxygen concentration device is mostly intended to be placed relatively close to the patient and is used continuously throughout the day by the patient regardless of dining or bedtime. Therefore, a noise generated from the oxygen concentration device is directly heard by the patient or patient's family, etc. and may give unpleasant feeling to them. There is concern that the noise has a significant influence particularly during sleep and the like by preventing the patient or the family from sleeping and thus negatively affecting their mental health. Sources of the noise generated by a pressure-swing absorption type oxygen concentration device include a structure-borne sound from a compressor for pressure variation, a suction sound and an exhaust sound from the compressor, an operating noise from a motor for driving the compressor, a purge gas flow noise of an adsorbent cylinder, and an operating noise from a cooling fan for the interior of the device housing. Among them, noises originated from the compressor such as the structure-borne sound radiation by the compressor, suction sound and exhaust sound of the compressor account for a large proportion of the whole device.

As described above, muffling the noise sources of the compressor is vital for the oxygen concentration device. A sound muffler called a cavity type or an expansion-chamber type has been used to reduce gas flow sounds such as the suction sound of the compressor and the like in a conventional oxygen concentration device. In addition to this, the sound muffler also needs to be miniaturized to realize a strong market demand of downsizing and weight reduction of the oxygen concentration device. For example, in a sound muffler described in Japanese Unexamined Patent Application Publication No. H10-245203, space saving is achieved by eliminating dead space by shaping the sound muffler into a cuboid and by integrating the sound muffler into an attachment part of the air filter.

However, the expansion-chamber muffler described above has such a feature that, as the ratio of the spatial cross-sectional area increases, the attenuation rate of the emitted sound increases, and the length of the cavity is related to the frequency of the sound desired to be reduced. Therefore, the physical size of the cavity is determined by the frequency band and the attenuation rate of the noise desired to be reduced, which is one of the obstacles for downsizing and weight reduction of the body of a low-noise oxygen concentration device.

In order to perform downsizing and weight reduction, while increasing the sound reducing effect of the sound muffler, Japanese Unexamined Patent Application Publication No. 2003-235982, for example, discloses a technique in which downsizing is maintained while serving sound attenuation by bringing an expansion-chamber muffler and a resonance muffler together and placing each muffler into the dead space.

As a sound muffler for attenuating a noise in high frequency band and low frequency band based on different principles, such technique as described in Japanese Unexamined Patent Application Publication No. 2005-6731 has been disclosed. In this technology, two sound mufflers are provided to reduce noises in high frequency band and low frequency band, where a long flow path is constituted using a sound-absorbing material for reducing the former, and this sound muffler is in turn incorporated in an expansion-chamber muffler for reducing the noise in the low frequency band, thereby achieving sound attenuation as well as downsizing and weight reduction. However, the expansion-chamber muffler requires the same size as before to reduce the noise in the low frequency band, and the fundamental technical problem remains unsolved. Furthermore, a conventional sound muffler needs to be connected to an intake port of a compressor, which is a vibrating body, through a pipe. Therefore, it becomes necessary to secure a structure, a space, and the like to isolate vibration, and there also arises a problem of space saving.

CITATION LIST

Japanese Unexamined Patent Application Publication No. H10-245203
Japanese Unexamined Patent Application Publication No. 2003-235982
Japanese Unexamined Patent Application Publication No. 2005-6731

SUMMARY OF INVENTION

Technical Problem

Recent oxygen concentration devices are required to satisfy improved noise reduction performance, and there is also a strong demand for downsizing and weight reduction for a portable application. In order to realize these, it is essential to improve performance of the sound muffler itself as well as to downsize the same. Under a circumstance where installation of an intake sound muffler is indispensable for reducing intake noise that is the largest noise source of the compressor, development of various sound mufflers is under way, but to separately install an intake sound muffler for noise reduction is a technical problem contradictory to downsizing of the oxygen concentration device.

The present invention provides a technology to realize noise reduction of the compressor itself, instead of installing a sound muffler, to suppress the intake noise generated by the compressor mounted on the oxygen concentration device.

Solution to Problem

The present inventors have found the following inventions related to a compressor as a method to solve such problems.
1. A compressor comprising a small chamber provided at an end part of a casing thereof, the small chamber comprising:
    a first lid part provided with a small hole forming an intake port for raw material air for the compressor, the first lid part constituting a portion of the casing of the compressor;
    a cylindrical part and;
    a second lid part forming the small chamber together with the first lid part and the cylindrical part,
    wherein an suction nozzle for introducing air into the small chamber is provided.
2. The compressor according to paragraph 1, wherein a filter is installed in the small chamber to divide the chamber into a compressor intake port side and the suction nozzle side.
3. The compressor according to paragraph 1, wherein the suction nozzle has a length of 100 mm or more.
4. The compressor according to paragraph 1, wherein the compressor is a reciprocating compressor and the casing is the cylindrical crank case.
5. An oxygen concentration device comprising:
    an adsorption cylinder packed with an adsorbent which selectively adsorbs nitrogen rather than oxygen,
    a compressor which supplies compressed air to the adsorption cylinder, and
    a flow path switching valve which switches a flow path between the compressor, adsorption cylinder, and a discharge pipe in order to repeat at a fixed timing a sequence of an adsorption step where the adsorption cylinder is pressurized, and adsorbs nitrogen in the compressed air and generates un-adsorbed oxygen; and a desorption step where the adsorption cylinder is evacuated to regenerate the adsorbent,
    wherein the compressor according to paragraph 1 is provided as the compressor.

Advantageous Effects of Invention

According to the present invention, it is possible to provide a compressor that can maintain muffling performance, and can be downsized and light-weighted.

DESCRIPTION OF EMBODIMENTS

The compressor of the present invention will be described in the following using drawings. In addition, the present invention is not restricted to such examples of embodiments.

Figure 1:
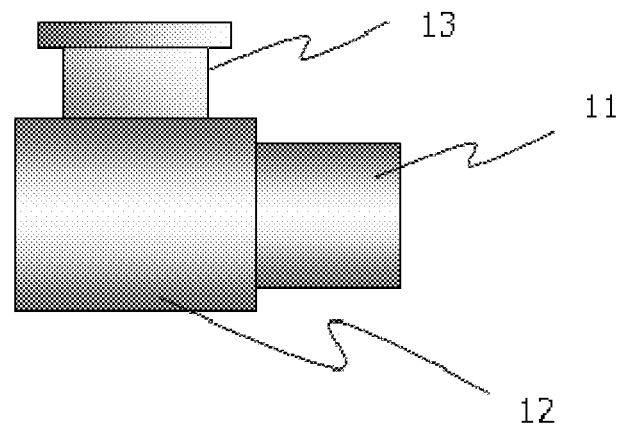
FIG. 1 is a schematic diagram of external appearance of a reciprocating compressor.

A reciprocating compressor shown in FIG. 1 comprising one piston-cylinder is a device that converts a rotational motion of a motor 11 into a reciprocating motion of a piston in a cylinder 13 via a crank part housed in a casing 12, and introduces outside air into the cylinder, and supplies the same as compressed air.

Figure 2:
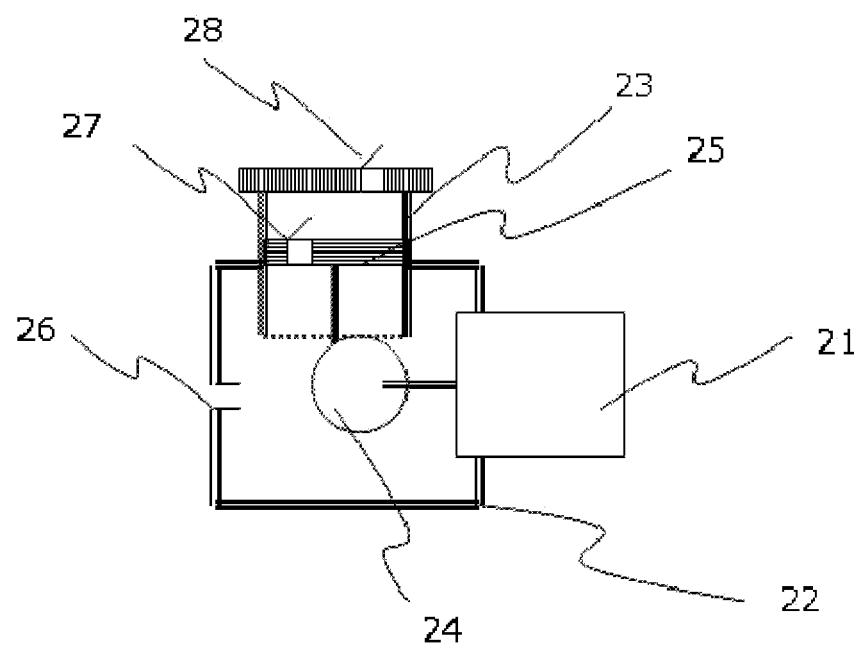
FIG. 2 shows a schematic diagram of a configuration of a conventional compressor.

As shown by a cross-sectional schematic diagram of FIG. 2, outside air taken in from an intake port 26 provided on a crank case 22 is transported as raw material air into a cylinder 23 via an intake valve 27 provided on a piston 25, compressed by a vertical motion of the piston 25, and supplied as compressed air from an exhaust valve 28 provided on an upper part of the cylinder. Even though most of noise generated by reciprocating motions of a crank part 24 which converts a rotational motion of the motor 21 into a reciprocating motion of the piston, and the piston 25 in the cylinder and, further by movements of intake and exhaust valves is confined in the case, a portion of the noise leaks outside from the intake port for introducing the raw material air, thus causing a problem of compressor noise.

Figure 3:
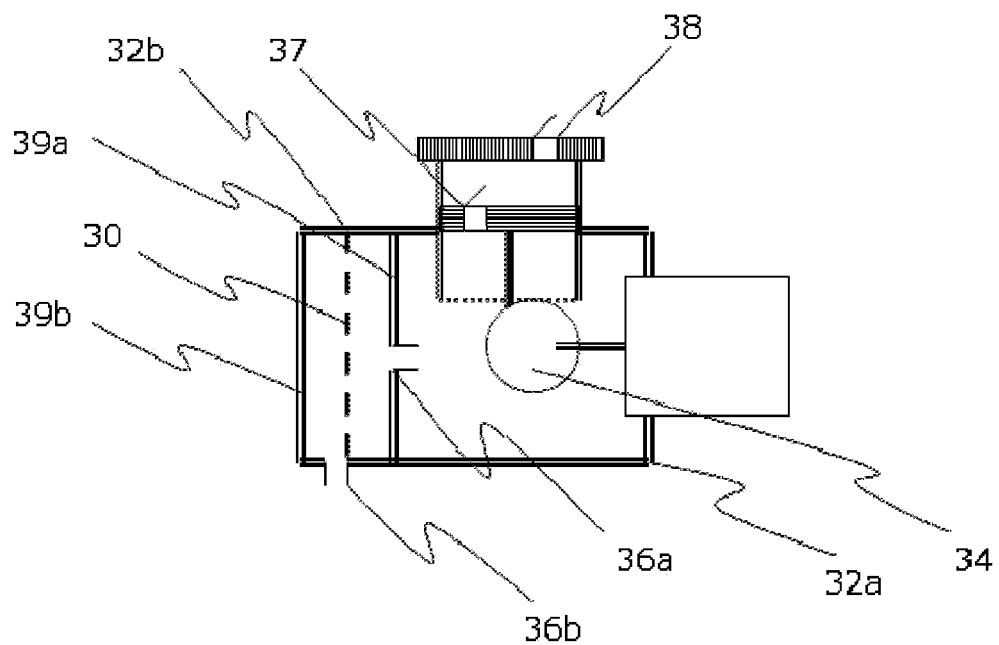
FIG. 3 shows a schematic diagram of a configuration of a compressor of an example of an embodiment of the present invention.

The compressor of the present invention is provided with a small chamber at an intake port side of a casing as shown in FIG. 3. Specifically, the small chamber is provided at an end of a cylindrical crank case 32a and is composed of a first lid part 39a provided with a conventional first intake port 36a, a second lid part 39b provided with a second intake port 36b which takes in outside air, and an extended cylindrical casing 32b and provided with a filter 30 inside.

Such a filter 30 plays a role of a dust-proof filter and by installing, for example, a nonwoven filter in such a small chamber, there can be prevented intrusion of foreign matter into the compressor. Furthermore, this works favorably for downsizing of the device as a whole. For example, installation of a separate intake filter in the intake piping, as has been the case in the past, becomes unnecessary. Such a dust-proof filter cannot be expected to exhibit a muffling effect and, when a fine-meshed sound absorbing material such as one having a muffling effect is installed, there are caused demerits such as a increase in an intake pressure and the like.

In order to enhance the muffling effect, openings of the first intake port 36a and the second intake port 36b are not arranged in a straight position but are arranged so that air flow has an angle of 90°. Thus, when the first intake port 36a is disposed at a center of the first lib part 39a, the second intake port 36b is disposed on the side of the cylindrical part 32b. Furthermore, by making a diameter of the small chamber 5 times or more, more preferably 10 times or more of a diameter of each intake port, there is exhibited an expansion-chamber type muffling effect.

Figure 4:
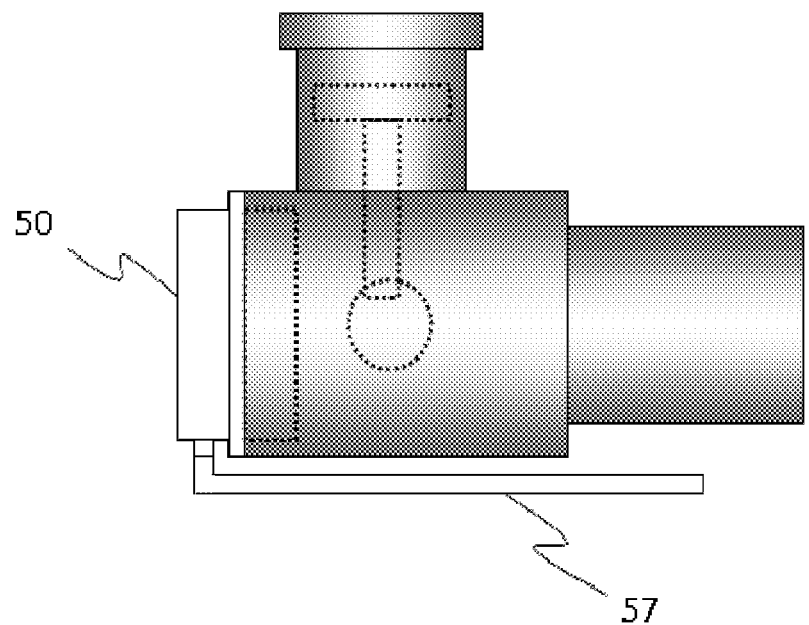
FIG. 4 shows a schematic diagram of external appearance of a compressor.

When outside air is taken in directly from the second intake port 36b, the compressor noise cannot be suppressed sufficiently. As shown in FIG. 4, it is important to install an suction nozzle 57 having a length of at least 100 mm. The longer the suction nozzle, the better the noise reduction effect is exhibited. However, when the nozzle is too long, an intake pressure increases, causing a decrease in an intake-air quantity. From the point of view of a balance between securing of a necessary quantity of intake-air and the noise reduction effect, it is preferable to use a nozzle length of 100 mm to 150 mm.

Figure 5:
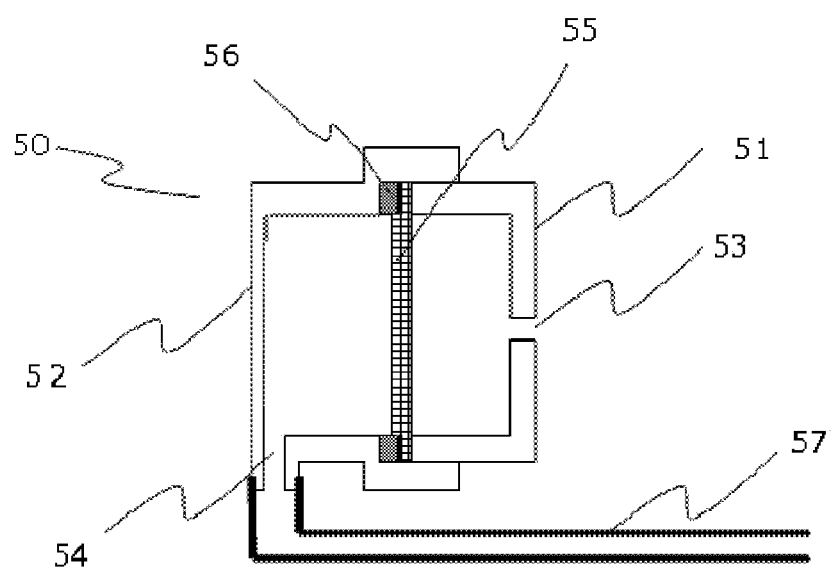
FIG. 5 shows a schematic diagram of a configuration of an intake muffling function part.

It is costly to fabricate a compressor casing itself such that it possesses a small chamber comprising the first lid part and the second lid part shown in FIG. 3. In the present invention, it is preferable to employ a structure such as shown in FIG. 5, where a cap structure having a filter installed inside is fitted at the end of a casing. A material of the structure body may be made of a metal such as aluminum and the like, as well as one made of a heat-resistant resin such as ABS and the like.

Specifically, as FIG. 5 shows constituent members, the compressor is configured by a first cap 51 having a first intake port 53 disposed at a center, a nonwoven filter 55, and a second cap 52 having a second intake port 54 provided on a side, which connects to an suction nozzle 57. The first cap 51 is provided with a lip to hold the filter 55 at a center and with a ring-shaped seal material 56. Raw material air taken in from the suction nozzle 57 can be introduced from the second cap 52 and, while maintaining a dust-free filter function by the filter 55, supplied into a compressor case from the first intake port 53 of the first cap 51.

The first cap is provided with an O-ring on the outer surface and, by fitting the first cap at the end of the cylindrical compressor case, the cap can be sealed at the end of the compressor casing. Thus, there can be produced simply and economically the compressor of the present invention having a small chamber provided with a muffling function and a dust-proof function.

Figure 6:
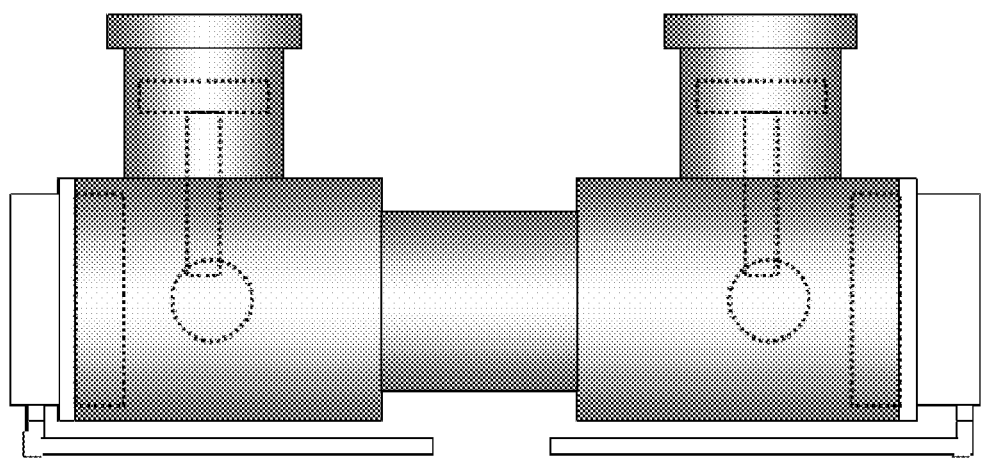
FIG. 6 shows a schematic diagram of configuration of a compressor of an example of another embodiment of the present invention.

In addition, even though the present invention has so far been described with a reciprocating compressor having one piston-cylinder as an example, the present invention can be applied along the same way of thinking to crank case parts of a reciprocating compressor provided with two piston-cylinders as described in FIG. 6.

When the noise reduction effects of the compressors of the present invention are compared, while the conventional reciprocating compressor shown in FIG. 2 provided with one piston-cylinder exhibits a noise level of 55 dBA, the compressor of the present invention shown in FIG. 3 exhibits a noise level of 50 dBA, corresponding to a noise reduction effect of 10%, and furthermore, the compressor shown in FIG. 4 equipped further with a 100 mm-long suction nozzle exhibits a noise level of 47 dBA, indicating a further noise reducing effect.

The compressor of the present invention can be applied to a pressure swing adsorption-type oxygen concentration device. The oxygen concentration device comprises a compressor which supplies compressed air, an adsorption cylinder packed with an adsorbent which selectively adsorbs nitrogen rather than oxygen, and a flow path switching means which switches a sequence of an adsorption step, a desorption step, a pressure equalizing step, and the like. An oxygen-concentrated gas generated by separation from the compressed air in the adsorption cylinder is, after being stored in a product tank for a while, adjusted to prescribed pressure and a prescribed flow rate by a pressure control valve and a flow rate control valve, and thereafter supplied from an oxygen outlet port to a user by means of a nasal cannula.

Raw material air brought into the device from outside contains about 21% oxygen, about 77% nitrogen, 0.8% argon, and 1.2% other gases such as carbon dioxide and the like. Such oxygen concentration device enriches only oxygen, which is essential for respiration, and extracts it.

To extract the oxygen-concentrated gas, the raw material air compressed by the compressor is supplied to an adsorption cylinder packed with an adsorbent formed of zeolite and the like, which selectively adsorbs nitrogen molecules rather than oxygen molecules, while switching the target adsorption cylinder sequentially by operating the supply and exhaust valves, and by selectively removing a nitrogen gas contained in the raw material air in the adsorption cylinder at a concentration of about 77%. As such an adsorbent, there can be used molecular sieve zeolite such as Type 5A, Type 13X, Type Li-X, and the like.

As such a compressor, there is used a reciprocating compressor such as a single head type shown in FIG. 4 provided with one piston-cylinder, or a double head type shown in FIG. 6 provided with two piston-cylinders. By so doing, a downsized and low-noise oxygen concentration device can be constituted without separately installing an intake sound muffler.

INDUSTRIAL APPLICABILITY

A compressor of the present invention possesses an intake muffling function and an intake filtering function by itself and, as a compressor that is light-weighted and downsized while maintaining reduced noise, can be used in medical devices such as a portable oxygen concentration device.

The invention claimed is:

1. A compressor comprising:
   a first lid part provided with a first intake port which forms an intake port of the compressor, the lid part constituting a portion of a cylindrical casing of the compressor;
   a cylindrical part; and
   a second lid part which forms a chamber together with the first lid part and the cylindrical part,
   wherein the cylindrical part is provided with a second intake port, and the second intake port is connected to a suction nozzle for sucking air into the chamber,
   wherein the second intake port is designed in such a way that the first intake port and the second intake port are arranged so that air flow has an angle of 90°,
   wherein a filter is installed in the chamber to divide the chamber into a compressor intake port side and the suction nozzle side,
   wherein the compressor is a reciprocating compressor and the casing is a cylindrical crank case, and
   wherein the compressor does not include a resonance muffler.

2. The compressor according to claim 1, wherein the suction nozzle has a length of 100 mm to 150 mm.

3. The compressor according to claim 1, wherein the chamber has a diameter which is 5 to 10 times of a diameter of each intake port.

4. A compressor consisting of:
   a cylindrical crank case;
   a motor;

a cylinder which is provided with an exhaust valve;

a piston which is housed in the cylinder and which is provided with an intake valve;

a crank part which is housed in the cylindrical crank case and which is connected to the motor and to the piston to convert a rotational motion of the motor to a reciprocating motion of the piston;

a first lid part provided with a first intake port which forms an intake port of the compressor, the lid part constituting a portion of the cylindrical crank case of the compressor;

a cylindrical part; and a second lid part which forms a chamber together with the first lid part and the cylindrical part, wherein the cylindrical part is provided with a second intake port, and the second intake port is connected to a suction nozzle for sucking air into the chamber, wherein the second intake port is designed in such a way that the first intake port and the second intake port are arranged so that air flow has an angle of 90°, wherein a filter is installed in the chamber to divide the chamber into a compressor intake port side and the suction nozzle side.

5. The compressor according to claim 4, wherein the suction nozzle has a length of 100 mm to 150 mm.

6. The compressor according to claim 4, wherein the chamber has a diameter which is 5 to 10 times of a diameter of each intake port.

7. A compressor consisting essentially of:

a first lid part provided with a first intake port which forms an intake port of the compressor, the lid part constituting a portion of a cylindrical casing of the compressor;

a cylindrical part; and a second lid part which forms a chamber together with the first lid part and the cylindrical part, wherein the cylindrical part is provided with a second intake port, and the second intake port is connected to a suction nozzle for sucking air into the chamber, wherein the second intake port is designed in such a way that the first intake port and the second intake port are arranged so that air flow has an angle of 90°, wherein a filter is installed in the chamber to divide the chamber into a compressor intake port side and the suction nozzle side, wherein the compressor is a reciprocating compressor and the casing is a cylindrical crank case.

8. The compressor according to claim 7, wherein the suction nozzle has a length of 100 mm to 150 mm.

9. The compressor according to claim 7, wherein the chamber has a diameter which is 5 to 10 times of a diameter of each intake port.

* * * * *